(12) United States Patent
Castro Rosas et al.

(10) Patent No.: US 10,849,322 B2
(45) Date of Patent: Dec. 1, 2020

(54) USE OF HIBISCUS ACID AND DERIVATIVES THEREOF AS ANTIMICROBIALS AGAINST ANTIBIOTIC-RESISTANT AND NON-ANTIBIOTIC-RESISTANT MICROORGANISMS

(71) Applicant: UNIVERSIDAD AUTONOMA DEL ESTADO DE HIDALGO, Hidalgo (MX)

(72) Inventors: Javier Castro Rosas, Hidalgo (MX); Carlos Alberto Gomez Aldapa, Hidalgo (MX)

(73) Assignee: Universidad Autinoma del Estado de Hidalgo, Hidalgo (MX)

( * ) Notice: Subject to any disclaimer, the term of this patent is extended or adjusted under 35 U.S.C. 154(b) by 0 days.

(21) Appl. No.: 16/062,437

(22) PCT Filed: Dec. 16, 2016

(86) PCT No.: PCT/MX2016/000147
§ 371 (c)(1),
(2) Date: Jun. 14, 2018

(87) PCT Pub. No.: WO2017/105211
PCT Pub. Date: Jun. 22, 2017

(65) Prior Publication Data
US 2019/0000080 A1 Jan. 3, 2019

(30) Foreign Application Priority Data
Dec. 16, 2015 (MX) .......................... A/2015/017439

(51) Int. Cl.
| | |
|---|---|
| *A01N 43/08* | (2006.01) |
| *C07D 307/33* | (2006.01) |
| *A61K 33/38* | (2006.01) |
| *A61K 31/365* | (2006.01) |
| *A61K 45/06* | (2006.01) |
| *A61K 33/18* | (2006.01) |

(52) U.S. Cl.
CPC ............ *A01N 43/08* (2013.01); *A61K 31/365* (2013.01); *A61K 33/18* (2013.01); *A61K 33/38* (2013.01); *A61K 45/06* (2013.01); *C07D 307/33* (2013.01)

(58) Field of Classification Search
CPC ...... A01N 43/08; A61K 31/19; A61K 31/215; A61K 31/39
USPC ....................................................... 424/618
See application file for complete search history.

(56) References Cited

FOREIGN PATENT DOCUMENTS

| | | | | |
|---|---|---|---|---|
| KR | 20070047743 A | * | 5/2007 | |
| WO | WO-2013183982 A1 | * | 12/2013 | ........... A23L 3/3472 |

OTHER PUBLICATIONS

Inês Da-Costa-Rocha et al. Food Chemistry 165 (2014) 424-443.*
Borrás-Linares I., Fernandez-Arroyo S., Arráez-Roman D., Palmeros-Suárez PA., Del Vaz-Díaz R., Andrade-Gonzáles I. et al. Characterization of phenolic compounds, anthocyanidin, antioxidant and antimicrobial activity of 25 varieties of Mexican Roselle (*Hibiscus sabdariffa*). Ind Crops Prod; Mar. 7, 2015. 69: 385-394.

* cited by examiner

*Primary Examiner* — Johann R Richter
*Assistant Examiner* — Courtney A Brown
(74) *Attorney, Agent, or Firm* — Defillo & Associates, Inc.; Evelyn A. Defillo

(57) ABSTRACT

The present invention relates to the use of compounds derived from calyces of Jamaica (*Hibiscus sabdariffa* L.) with antimicrobial activity, which can be used in different areas of microbiology, such as, for example, medical microbiology, veterinary microbiology, industrial microbiology, environmental microbiology, marine microbiology, plant microbiology, food microbiology and biotechnology; more particularly, to the individual use of *Hibiscus* acid and its derivatives as antimicrobials and its uses in effective formulation to eliminate bacteria of all types of living or inert materials.

1 Claim, 6 Drawing Sheets

USE OF HIBISCUS ACID AND DERIVATIVES THEREOF AS ANTIMICROBIALS AGAINST ANTIBIOTIC-RESISTANT AND NON-ANTIBIOTIC-RESISTANT MICROORGANISMS

TECHNICAL FIELD OF THE INVENTION

The present invention relates to the use of compounds derived from calyces of Jamaican sorrel (*Hibiscus sabdariffa*) with antimicrobial activity, which can be used in different areas of microbiology, such as, for example, medical microbiology, veterinary microbiology, industrial microbiology, environmental microbiology, marine microbiology, plant microbiology, food microbiology and biotechnology. The invention relates more particularly to the individual use of *Hibiscus* acid and the derivatives thereof as antimicrobials, and to the uses thereof in an effective formulation for eliminating all types of bacteria from living or inert materials.

BACKGROUND ART

Calyces of the plant known in Mexico as Jamaica (*Hibiscus sabdariffa* L.) have been commonly used as a food either alone in beverages, or mixed with other herbs, they have also been used as hot or cold beverages, as a flavoring agent in the industry of food and as medicine. Numerous studies have been carried out both in vitro and in vivo of the extracts of the calyces of Jamaica and of some of their components with the purpose of determining different properties with effect in animal subjects. Different chemical compounds present in the calyces of Jamaica have also been identified, such as, for example, *Hibiscus* acid and its derivatives. Both *Hibiscus* acid and its derivatives are currently used in the field of medicine and biotechnology with different uses, to exemption as antimicrobial.

Currently, it is necessary to have new options for non-toxic antimicrobials for use in different areas of microbiology due to the adaptation or resistance that the bacteria acquire against the antimicrobials currently in use, such as antibiotics.

It is known that plants have a large number of substances that inhibit various metabolic activities of bacteria, yeasts and molds, inactivating them (Tajkarimi el al., 2010; Cruz-Galvez, 2013). These compounds from plants could be used for the manufacturing of new drugs or formulations with greater effectiveness to inhibit or eliminate both resistant and non-resistant bacteria to antimicrobials, such as antibiotics, for example.

The acid *Hibiscus* and its derivatives from the calyces of Jamaica (*Hibiscus sabdariffa* L.) could be used like antimicrobials with application in the different areas of the microbiology.

Currently, no antimicrobial effect of *Hibiscus* acid or its derivatives has been reported in the art, so this is the main novelty of the present invention.

As background of the present application, we have evaluated the antimicrobial effect of extracts of calyces from Jamaica with different polarities obtained from the calyces of the flower of Jamaica against different pathogenic microorganisms (Morales-Cabrera, et al., 2010). And it has been found that all the extracts obtained show an antimicrobial effect against all the microorganisms tested (Gutiérrez-Alcántara et al., 2015).

However, prior to the present invention there were no specific studies showing which of the molecules or chemical compounds are directly responsible for the antimicrobial effect observed in the calyces of Jamaica.

Few patent documents describe extracts of the calyces of the flower of Jamaica (*Hibiscus sabdariffa* L.) and its use as material with antimicrobial properties.

Applicants have previously filed seven patent applications on different and specific compositions that can be used as disinfectants for specific fruits and vegetables.

For example, patent application MX/a/2012/006393 describes the use of formulations containing mixtures of aqueous extract of calyces from Jamaica (at 1%), acetic acid (between 0.1 and 0.5%) and sodium hypochlorite (100 mg/L) developed to specifically disinfect seeds intended for the production of sprouts for human consumption. These compositions are effective in eliminating pathogenic bacteria of intestinal origin and which are pathogenic to humans, such as *Salmonella* and £ *coli* O157: H7, for example.

Patent application MX/a/2013/014625 describes the use of acetone extract mixtures of calyces from Jamaica (at 1%), acetic acid (between 0.1 and 0.5%) and sodium hypochlorite (100 mg/L) developed for disinfect green chiles specifically. These compositions are effective only for green chile. And they have been developed to eliminate pathogenic bacteria of intestinal origin and which are pathogenic to humans, such as *Salmonella* and *E. coli* O157: H7, for example.

Patent application MX/a/2013/014626 describes the use of mixtures of an aqueous extract of calyces from Jamaica (at 1%), acetic acid (between 0.1 and 0.5%), sodium hypochlorite (between 50 and 100 mg/L) and polysorbate 80 (at 2%) and that have been developed to specifically disinfect lettuce. These compositions are effective only for disinfecting lettuce. And they have been developed to eliminate from the lettuce pathogenic bacteria of intestinal origin and that are pathogenic for the human.

Patent application MX/a/2013/014627 describes the use of acetone extract mixtures of calyces from Jamaica (at 1%), acetic acid (between 0.1 and 0.5%), sodium hypochlorite (100 mg/L) and polysorbate 80 (to 2%) and that have been developed to specifically disinfect apples. These compositions are effective only for disinfecting apples. These formulations have been developed to eliminate from the apples pathogenic bacteria of intestinal origin and that are pathogenic for humans.

Patent application MX/a/2013/014628 describes the use of formulations containing mixtures of a methanolic extract of calyces from Jamaica (at 1%), acetic acid (between 0.1 and 0.5%), sodium hypochlorite (100 mg/L) and polysorbate 80 (at 2%) and which have been developed to specifically disinfect tomatoes (red tomatoes). These compositions are effective only for disinfecting tomatoes. These compositions have been developed to eliminate from the tomatoes pathogenic bacteria of intestinal origin and which are pathogenic for humans.

Patent application MX/a/2013/014629 describes the use of different formulations: a) mixtures of a methanolic extract of calyces from Jamaica (at 1%), a chromatographic fraction obtained from an acetone extract of calyces from Jamaica (at 1%)), acetic acid (between 0.1 and 0.5%), sodium hypochlorite (100 mg/L) and polysorbate 80 (at 2%); b) mixtures of a methanolic extract of calyces from Jamaica (at 1%), a chromatographic fraction obtained from a methanolic extract of calyces from Jamaica (at 1%), acetic acid (between 0.1 and 0.5%), sodium hypochlorite (100 mg/L) and polysorbate 80 (at 2%). These formulations have been developed to specifically disinfect cilantro. These compositions are effective only for disinfecting cilantro. These compositions have been developed to eliminate from the cilantro pathogenic bacteria of intestinal origin and which are pathogenic for humans.

Patent application MX/a/2014/015503 describes the use of mixtures of a specific chromatographic fraction obtained from an acetone extract of calyces from Jamaica mixed with a specific fraction obtained from a methanolic extract of mixed calyces from Jamaica, acetic acid (between 0.1 and 0.5%), sodium hypochlorite (100 mg/L) or calcium hypochlorite (100 mg/L) and polysorbate 80 (at 2%). These formulations have been developed to disinfect fruits, such as tomato or chili.

An important fact is that the 7 patent applications prior to this contain mixtures of different components of the calyces of Jamaica and in no application is specified the name or chemical structure of some compound from the calyces of Jamaica as responsible for the observed antimicrobial effect, since in such inventions such specific compounds were not elucidated.

The patent application JP2002128602 describes its use in an agrochemical composition to protect plants in fields of crops, while the application US20100323046 describes the use of a crude extract of the calyces of Jamaica to produce a medicine to treat urinary infections caused by *Escherichia coli* and *Candida albicans*.

In the patent application KR20080092186 an extract of Jamaica is described which is used to improve the quality of the beef, pork and chicken meat and to increase its storage stability. The extract is prepared by extraction with ethanol and subjected to a cold drying process. The concentration of the extract in the composition is 500 mg/ml and the meat is treated with a preparation of 0.5 to 3.0% (by weight).

On the other hand, in the application US20120015062 there are described compositions comprising an extract of the plant *Agapanthus africanus* and compositions comprising this extract plus other extracts of other different plants, such as for example plants of the Rosa or alfalfa family to be used as agents in the biological protection of other plants including their seeds. Although in this patent application document reference is made to the article published by Leksomboon et al. (Kasetsart, Journal Natural Science 35: 392-396, 2001.) where it is mentioned that extracts obtained from different plants (*Hibiscus sabdariffa* L., *Psidium guctjava, Punic granatum, Spondias pinnata* and *Tamarindus indica*) have an antimicrobial function, said document does not contribute any experimental evidence that involves the extracts of *Hibiscus sabdariffa* for the same use that is given to extracts of *Agapanthus africanus*.

BRIEF DESCRIPTION OF THE FIGURES

Other advantages of the present invention are readily appreciated as the same becomes better understood by reference to the following detailed description when considered in connection with the accompanying drawings wherein.

SUMMARY OF THE INVENTION

Figure 1:
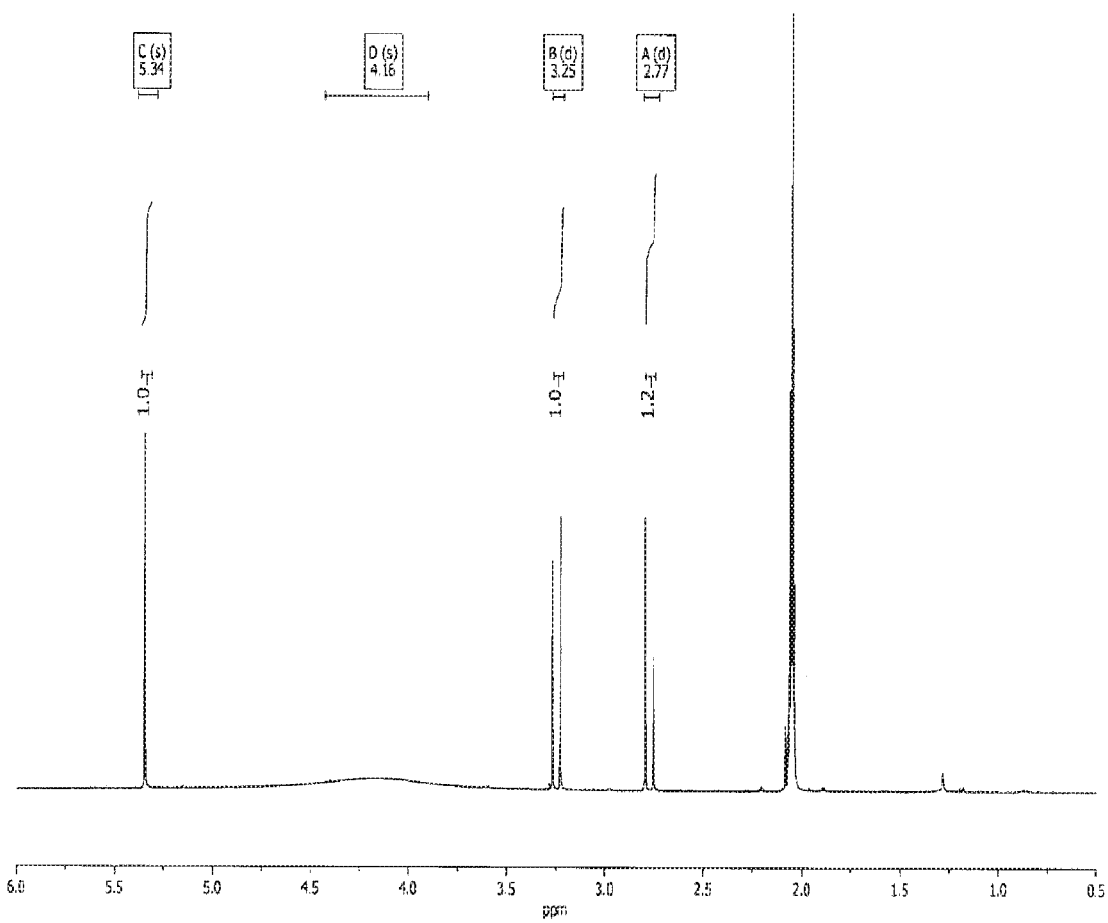
FIG. 1 shows a nuclear magnetic resonance (NMR) spectrum of PROTON (1H) of *Hibiscus* acid.

In accordance with the problems mentioned above, there is provided new effective antimicrobials to inactivate or eliminate resistant pathogenic microorganisms and not resistant to antibiotics of all types of living or inert materials, even under extreme conditions of treatment, either by their use alone or in formulations with known components and that are not toxic to the environment, plants or animal subjects.

The present invention relates to the use of *Hibiscus* acid and its derivatives obtained from the calyces of the flower of Jamaica (*Hibiscus sabdariffa* L.) or by chemical synthesis, which are used as antimicrobials in all types of living or inert materials.

One embodiment of the present invention relates to formulations containing *Hibiscus* acid or its derivatives isolated from the calyces of the flower of Jamaica (*Hibiscus sabdariffa* L.) or by chemical synthesis, by methods known in the art, which are useful for eliminating pathogenic bacteria resistant and not resistant to antibiotics present in living or inert materials.

One embodiment of the present invention relates to formulations containing *Hibiscus* acid and/or its derivatives isolated from extracts of extracts of different polarities obtained from the calyces of the flower of Jamaica (*Hibiscus sabdariffa* L.) or by chemical synthesis, by any of the methods existing in the art, preferably obtained by chromatography, and which are useful for eliminating resistant pathogenic bacteria and non-resistant to antibiotics of living or inert materials.

Another embodiment of the present invention relates to obtaining *Hibiscus* acid and its derivatives from the calyces of the flower of Jamaica (*Hibiscus sabdariffa* L.) or by chemical synthesis, and which are used as antimicrobials against resistant and non-resistant pathogenic microorganisms to antibiotics present in live or inert materials, which are innocuous, which are an alternative to the use of conventional antimicrobials, such as antibiotics, disinfectants and preservatives, which have limited effectiveness or can be toxic to plants, animals, human or to the environment.

Another embodiment of the present invention relates to the preparation of compositions containing *Hibiscus* acid or its derivatives obtained from the calyces of Jamaica (*Hibiscus sabdariffa* L.) or by chemical synthesis having an antimicrobial function together with other compounds having antimicrobial properties, for example, antibiotics, disinfectants or preservatives.

The use of *Hibiscus* acid and its derivatives as antimicrobials, disinfectants or preservatives obtained from the calyces of Jamaica or by chemical synthesis, is another embodiment that is described in the present invention.

*Hibiscus* acid and its derivatives from the calyces of Jamaica or chemical synthesis, can be useful in the development of drugs, bioactive compounds, disinfectants or preservatives efficient to eliminate pathogenic bacteria resistant and not resistant to antibiotics present in living or inert materials.

Unlike other compounds or compositions known up to know for the same purpose, the compounds or molecules of the present invention are capable of eliminating resistant pathogenic bacteria and non-resistant to antibiotics present in living or inert materials without health effect, or without altering its properties or the quality characteristics of the product. In addition, the compounds of the present invention are known in the art, which guarantees that the antimicrobial, disinfectant, preservative effect is constant and can be quantified.

DETAILED DESCRIPTION OF THE INVENTION

The compounds of the present invention include molecules obtained from the calyces of Jamaica or by chemical synthesis, which had not been reported in the art as compounds with antimicrobial activity, such as, for example, *Hibiscus* acid, mono- and di-methyl-ester of *Hibiscus* acid, mono- and di-ethyl ester of *Hibiscus* acid; mono- di- and tri-ethylester of hydroxycitric acid, which can be used alone or in combination with other compounds having antimicrobial properties, for example antibiotics, disinfectants or preservatives.

For purposes of the present invention, the compounds described herein, include: Compounds derived from plant extracts, which exhibit antimicrobial properties, such as, for example, *Hibiscus* acid, the mono- and di-methyl ester of *Hibiscus* acid, mono- and di-ethyl ester of *Hibiscus* acid; mono- di- and tri-ethylester of hydroxycitric acid and mixtures thereof, obtained from calyces of Jamaica (*Hibiscus sabdariffa* L.) or by chemical synthesis, in a w/w concentration from 0.01% to 10%, preferably from 0.1% to 5%.

For purposes of the invention, the compositions are added to materials to be treated by methods known in the art, such as direct application, intramuscular, intravenous, oral, peritoneal application, through aerosols, the complete immersion of the material in the solutions antimicrobial or by means of devices that allow their adequate dispersion in the materials to be treated. The compositions of the invention can be added or contacted with the materials in an amount of 0.01 per 1 Kg of material, preferably 0.1 to 1 g per 100 g of material, or to be added in larger volumes according to the needs of the antimicrobial in the material. After being applied, the compositions can remain the necessary time until obtaining the desired antimicrobial effect in the material.

The compounds described herein can be sterilized or not sterilized and stored at room temperature, whereby they are ready to be applied to the materials when deemed necessary.

For purposes of the invention, the compounds described herein refer to *Hibiscus* acid, the mono- and di-methyl ester of *Hibiscus* acid, mono- and di-ethyl ester of *Hibiscus* acid; mono- di- and tri-ethylester of hydroxycitric acid and mixtures thereof, obtained from calyces of Jamaica (*Hibiscus sabdariffa* L.) or by chemical synthesis, which are put in contact with the materials, for example, plants, subjects animals and inert materials, with the purpose of disinfecting or preserving them, or providing an alternative antimicrobial to antibiotics. In the present invention, the disinfecting activity of *Hibiscus* acid, the mono- and di-methyl ester of *Hibiscus* acid, mono- and di-ethyl ester of *Hibiscus* acid; mono- di- and tri-ethylester of hydroxycitric acid and mixtures thereof, obtained from calyces of Jamaica or by chemical synthesis, as support in the disinfection and or preservation of different materials, antimicrobial alternative to antibiotics, for example, plants, animal subjects and inert materials, so they can be used directly or as part of compositions that contain them. In this sense, *Hibiscus* acid, the mono- and di-methyl ester of *Hibiscus* acid, mono- and di-ethylester of *Hibiscus* acid, mono- di- and tri-ethyl ester of hydroxycitric acid derived from the calyces of Jamaica or synthesis chemical, can be administered, added or put in contact with the materials to be treated in a concentration w/w of 0.001% to 10%, preferably from 0.1% to 1%.

The antimicrobial effectiveness in living or inert materials of the compounds described herein is such, that it inactivates or eliminates bacteria that are both resistant and non-resistant to antibiotics that may be present in them, without affecting health, nor the properties or the quality characteristics of the product.

*Hibiscus* acid and its derivatives such as the mono- and di-methyl ester of *Hibiscus* acid, mono- and di-ethylester of *Hibiscus* acid, mono- di- and tri-ethylester of hydroxycitric acid, can be obtained from the calyces of Jamaica (*Hibiscus sabdariffa* L.) or chemical synthesis, by different methods known in the art.

The present invention constitutes the first report of the antimicrobial activity of *Hibiscus* acid and its derivatives, so it can be used alone or in combination with other antimicrobials, in the treatment of living or inert materials. As will be seen below, the compounds of the invention are capable of eliminating resistant and non-resistant microorganisms to antibiotics in a very efficient way, with which it is possible to count on antimicrobials, effective, of natural origin, innocuous and non-toxic.

The following examples are included below for the sole purpose of illustrating the present invention, without implying any limitation within its scope.

Example 1: Materials and Methods 1.1 Vegetal Material:

Calyces dry of Jamaica (*Hibiscus sabdariffa* L.) of the variety criolla from Oaxaca, Mexico.

1.2 Bacterial Strains:

Use strains of *Escherichia coli* 0157: H7, *E. coli* enteroinvasive, *E. coli* enterotoxigenic, *E. coli* enteropathogenic, *Salmonella Typhimurium* R+(multiresistant strain of 14 antibiotics isolated from raw meat) *Salmonella choleraesuis* (ATCC 10708), *Listeria monocytogenes* (ATCC 19115), *L. monocytogenes* scott A, *Staphylococcus aureus* (ATCC 25923), *Pseudomonas aeruginosa* (ATCC 27853), *Shigella sonnei* (ATCC 25931) and *Shigella flexneri* (ATCC 12022), *V. cholerae* 01 (serotype Inaba) and *Pseudomonas aeruginosa* (ATCC 27853). Select mutants resistant to the antibiotic rifampicin (R+) to eliminate the interference of the native microbial flora of *Hibiscus* acid and derivatives (Castro-Rosas and Escartín, 2000). Maintain the R+ strains at 4-7° C. on blood-based agar (ABS, Merck®, Germany) with biweekly transfers, activating tripticasein soy broth (CST, Bioxon®, Mexico) with incubation at 35° C./24 h.

1.3 Preparation of the Compounds: *Hibiscus* Acid, Mono- and Di-Methyl Ester of *Hibiscus* Acid, Mono- and Di-Ethyl Ester of *Hibiscus* Acid, Mono- Di- and Tri-Ethylester of Hydroxycitric Acid, from Calyces Extract from Jamaica by Chromatography in Column:

Distribute 1000 g of calyces from Jamaica in flasks and add methanol, or acetone, or ethanol in a 1:9 ratio and grind in a blender. Store the ground mixture for seven days at room temperature. Filter later with a No. 200 sieve (MONTIMAX) to remove particles. Then remove the solvent from the extract with a rotary evaporator (Buchi R-205) using the following conditions: temperature of 40° C. of the tub, rotation of 80 rpm and vacuum pressure of 72 mbar. Recover the dry extract in dry containers and store at room temperature until use.

Separate the extract into fractions using the column chromatography technique. Use silica gel previously activated at 120° C. Mix the silica gel with the dry extract until complete homogenization using methanol, or acetone or ethanol as a humectant. Mount a chromatographic column; for this, place a small piece of cotton at the bottom of the column with the help of a rod. Then place the column on a universal support ensuring that the column is straight.

The next step is to mix the silica gel with hexane, until a smooth paste is obtained; Then pour into the column until it reaches the desired level and then add hexane to prevent the silica from drying out. Then add all the extract little by little; then place a small layer of calcium sulphate (drying) on the extract and place a layer of cotton. Then fill the column with the solvent (hexane) and lower the fractions with the different solvent mixtures using mixtures of hexane, hexane acetate, acetate-methanol and methanol as shown in Table 1; Recover each fraction in 50 ml quantities. Subsequently, remove the solvent from each fraction recovered with a rotary evaporator and perform thin layer chromatography of each dry fraction. Finally, gather in groups or collections the fractions that present a similar chromatogram.

1.4 Determination of the Antimicrobial Activity of the Corresponding Fractions from the Methanolic Extract of Calyces of Jamaica in Culture Medium (In Vitro Studies):

1.4.1 Preparation of the Inoculum of the Strains:

Prepare cultures of each one of the R+ study bacteria in tubes of 13×100 mm containing 3 ml of Tripticasein Soy Broth (TSB) incubating at 35° C. for 24 hours. Subsequently, centrifuge the cultures at 3500 rpm for 20 minutes. Then discard the supernatant and resuspend the cell pack by adding 3 ml of sterile isotonic saline solution (ISS) and agitate in vortex for 10 seconds. Repeat the previous procedure two more times. Subsequently, dilute each culture of the washed strains in a decimal proportion with ISS.

1.4.2 Preparation of the Solutions with Chromatographic Fractions:

From the dry fractions (collections) prepare aqueous solutions using a solution of Polysorbate 80:water that was previously prepared in a ratio of 20:80. To this solution of polysorbate 80:water, add each dry fraction or chromatographic collection separately in a 1:9 ratio, in clean jars.

TABLE 1

Solvents and mixtures used to obtain fractions from the extract of the calyces of Jamaica

| | Solvent | Concentration |
|---|---|---|
| (−) | Hexane | 100% |
| ↑ | Hexane-Acetate | 90-10% |
| | Hexane-Acetate | 80-20% |
| | Hexane-Acetate | 70-30% |
| | Hexane-Acetate | 60-40% |
| | Hexane-Acetate | 50-50% |
| | Hexane-Acetate | 40-60% |
| | Hexane-Acetate | 30-70% |
| | Hexane-Acetate | 20-80% |
| | Hexane-Acetate | 10-90% |
| Polarity | Acetate | 100% |

TABLE 1-continued

Solvents and mixtures used to obtain fractions from the extract of the calyces of Jamaica

| | Solvent | Concentration |
|---|---|---|
| | Acetate-Methanol | 90-10% |
| | Acetate-Methanol | 80-20% |
| | Acetate-Methanol | 70-30% |
| | Acetate-Methanol | 60-40% |
| | Acetate-Methanol | 50-50% |
| | Acetate-Methanol | 40-60% |
| | Acetate-Methanol | 30-70% |
| | Acetate-Methanol | 20-80% |
| | Acetate-Methanol | 10-90% |
| ↓ | | |
| (+) | Methanol | 100% |

1.4.3 Identification of *Hibiscus* Acid and its Derivatives:

1.4.4 Antimicrobial Effect of the Fractions in Culture Medium:

Separately, place 100 µL of the first dilution of the washed and diluted cultures on boxes of Agar Soya Tripticasa (AST) supplemented with 100 mg/L of the antibiotic rifampin; distribute the inoculum over the entire surface of the agar using the surface extension technique. Place on the inoculated boxes, separately, filter paper discs of a size of 0.5 cm and on the disks place aliquots of 10 µL of the solution of the chromatographic fractions. Perform four repetitions for each treatment. After the aliquots of the fractions or collections are absorbed by the agar, incubate the culture boxes at 35° C. for 24 hours.

Choose the chromatographic collections that show an inhibitory effect in culture medium against all the study bacteria. Separate the compounds by re-chromatography on a column (second chromatography) and thin layer chromatography. Determine the antimicrobial effect in culture medium of the new fractions obtained from this second re-chromatography, against all the study bacteria in the same way as described above. Perform nuclear magnetic resonance (NMR) analysis of the fractions that show an antimicrobial effect in culture medium.

With the help of the resonance equipment software, elucidate the structure of the molecules responsible for the antimicrobial effect. The general procedure to perform the NMR analysis is described below.

1.5 Nuclear Magnetic Resonance (NMR) of Chromatographic Fractions:

Determine the NMR spectrum of the proton (1H) and carbon 13 (13C) of the antimicrobial fractions obtained from the second chromatography from fractions chromatographic with antimicrobial activity obtained from the first chromatography of the methanolic, acetonic and ethanolic extract. Solubilize the fractions in deuterated water or deuterated chloroform (Sigma, Mexico). Analyze the solubilized samples using a nuclear magnetic resonance spectrometer (Varian NMR, 400 MHz). Perform the elucidation of the molecular structures from the spectrograms obtained with the help of the MestReNova program. Finally, separate in clean containers the samples or fractions where the *Hibiscus* acid and its derivatives are identified.

Example 2: Collections of Fraction Chromatographs Obtained

In total, 584 fractions (Table 2) of the methanolic extract, 560 of the acetonic extract and 600 of the ethanolic extract were obtained. The recovered fractions were collected in collections using the thin-layer chromatography technique. In total, the methanolic extract obtained 23 collections, from the acetonic

Example 3: Antimicrobial Activity of Fraction Collections

Of all the collections obtained (62) from the chromatography of the methanolic, acetonic and ethanolic extracts, only 20 showed antimicrobial activity against the study pathogens (data not shown). And of these 20 collections only 10 were those that exhibited greater areas of inhibition with a size between 4 and 5 mm larger areas than those caused by the other fractions (between 14 to 18 mm in diameter). Consequently, these 10 collections of fractions (4 of the methanolic extract, 3 of the acetonic and 3 of the ethanolic extract) underwent a second chromatography to obtain purer compounds for analysis by the NMR technique.

TABLE 2

Example of fractions obtained from the methanolic extract of the calyces of Jamaica

| Fraction | Solvent concentration |
| --- | --- |
| 1-28 | Hexane 100% |
| 29-73 | Hexane 90% - Ethyl acetate 10% |
| 74-149 | Hexane 80% - Ethyl acetate 20% |
| 150-213 | Hexane 70% - Ethyl acetate 30% |
| 214-257 | Hexane 60% - Ethyl acetate 40% |
| 281-296 | Hexane 50% - Ethyl acetate 50% |
| 297-321 | Hexane 40% - Ethyl acetate 60% |
| 322-361 | Hexane 30% - Ethyl acetate 70% |
| 362-421 | Hexane 20% - Ethyl acetate 80% |
| 422-450 | Hexane 10% - Ethyl acetate 90% |
| 451-497 | Ethyl acetate 100% |
| 498-584 | Ethyl acetate 90% - Methanol 100% |

Example 4: Antimicrobial Fractions Obtained from the Second Re-Chromatography From each of the collections that underwent re-chromatography in column, 10 fractions (30 fractions in total) were obtained, which were analyzed by nuclear magnetic resonance.

Figure 2:
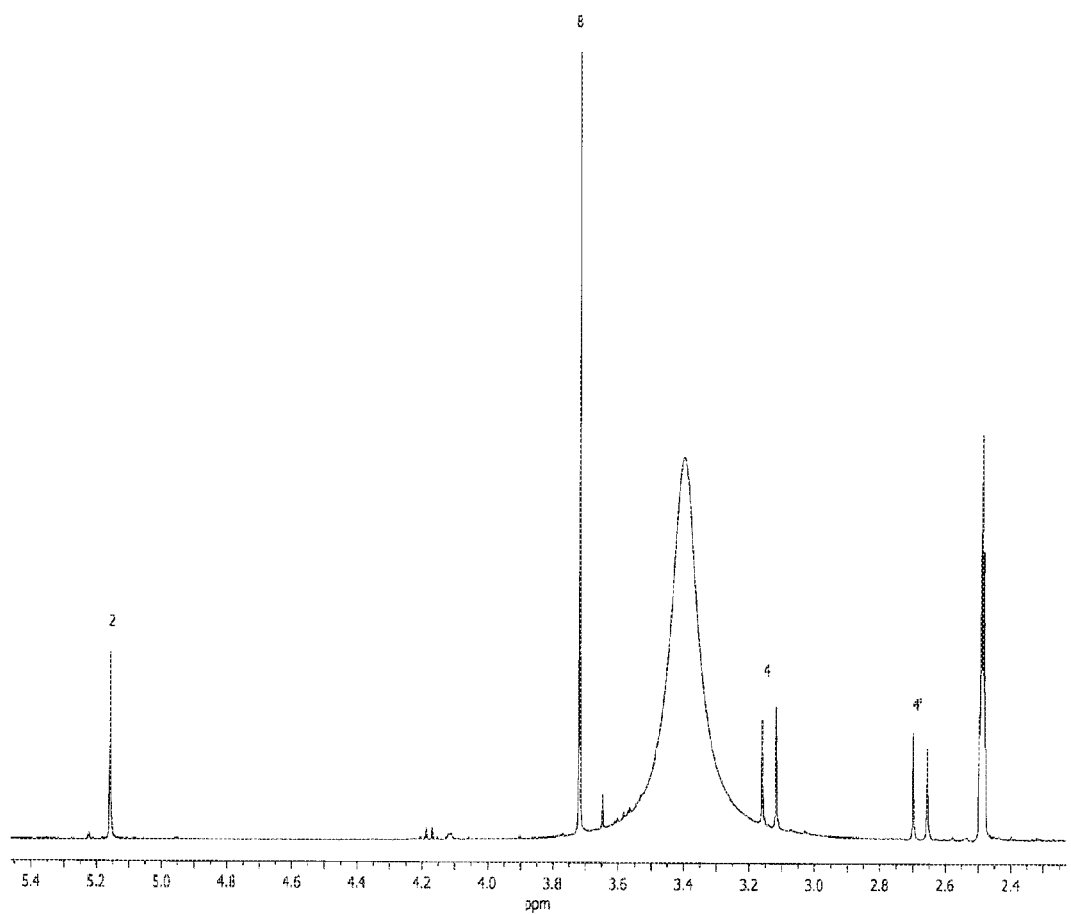
FIG. 2 shows a nuclear magnetic resonance (NMR) spectrum of PROTON (1H) of the methyl monoester of *Hibiscus* acid.
Figure 3:
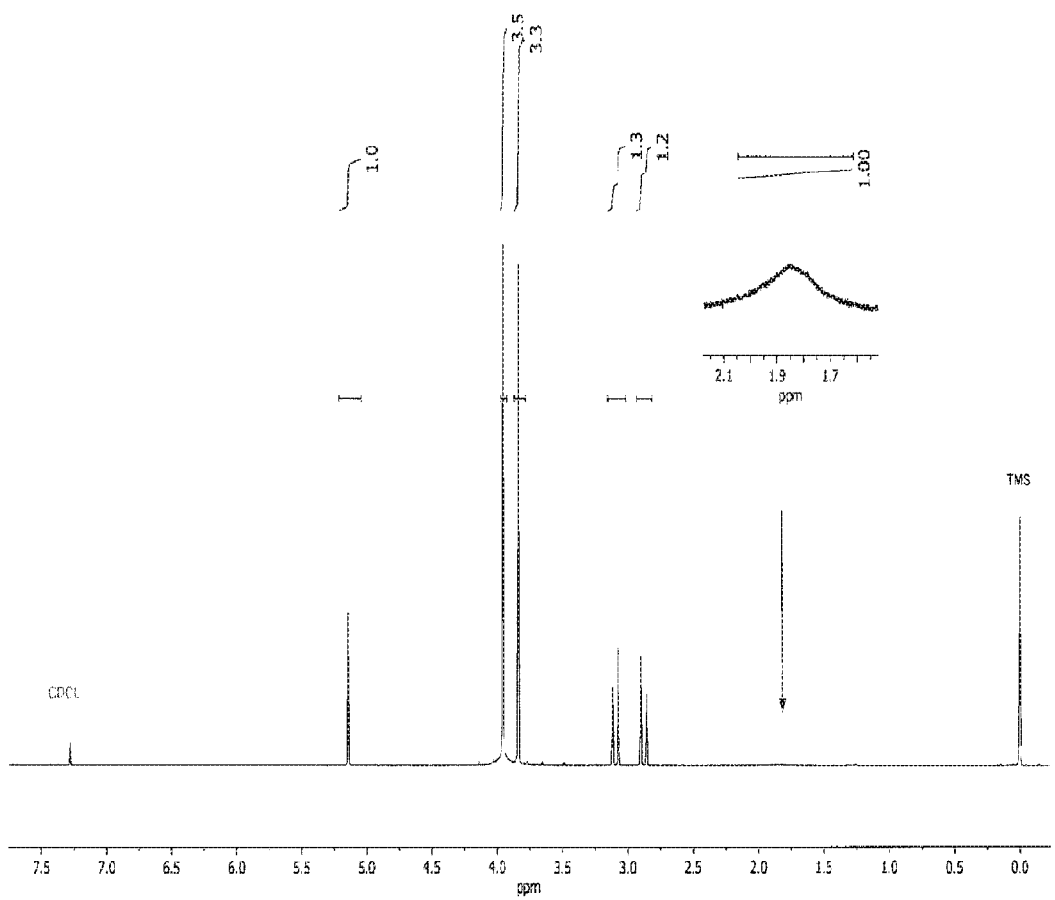
FIG. 3 shows a nuclear magnetic resonance spectrum (NMR) of PROTON (1H) of the methyl diester of *Hibiscus* acid.
Figure 4:
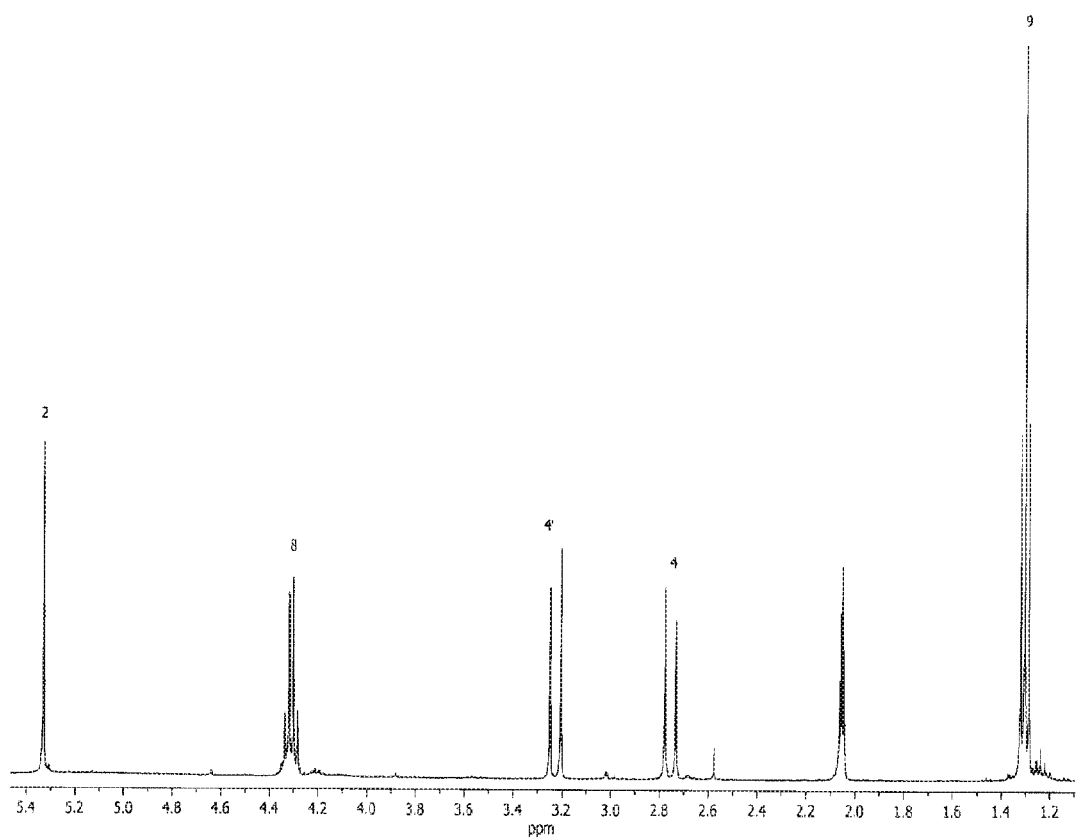
FIG. 4 shows a nuclear magnetic resonance spectrum (NMR) of PROTON (1H) of the ethyl monoester of *Hibiscus* acid in acetone-d6.
Figure 5:
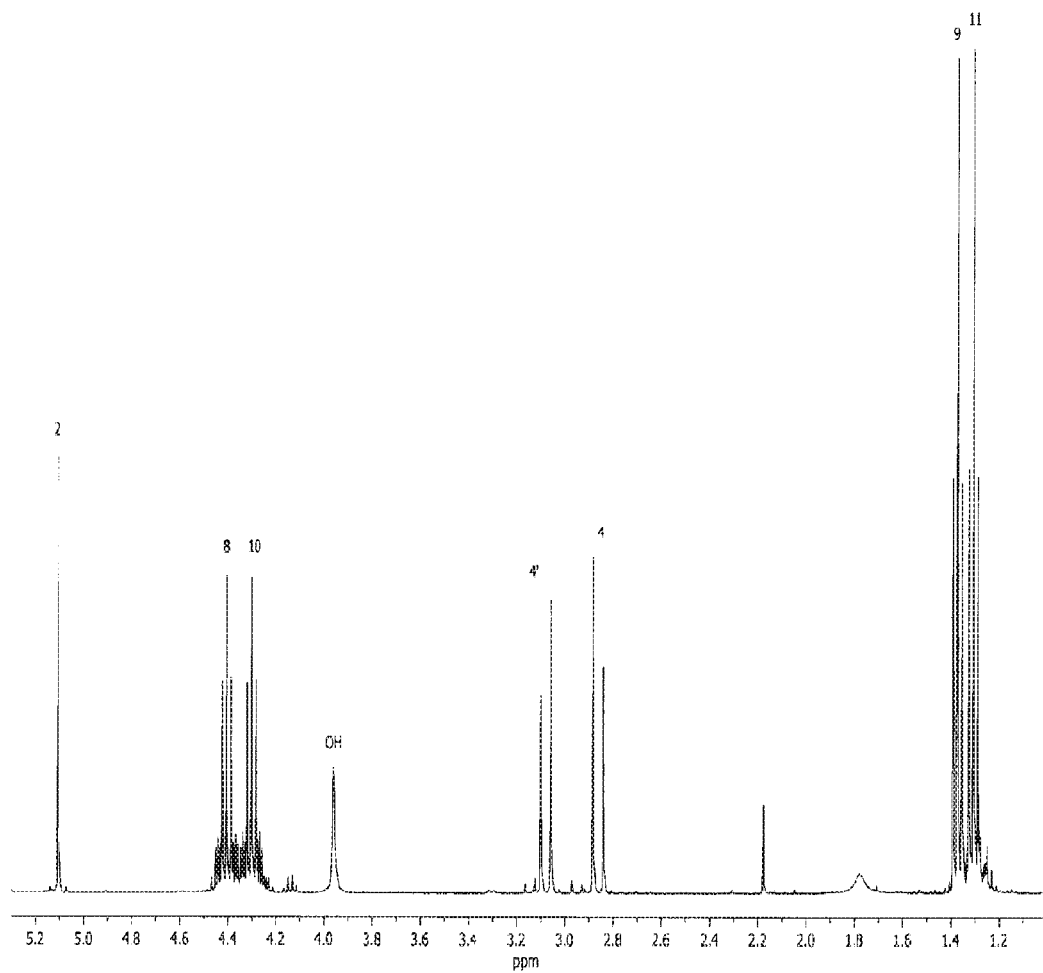
FIG. 5 shows nuclear magnetic resonance spectrum (NMR) of PROTON (1H) of the ethyl diester of *Hibiscus* acid in acetone-d6 is shown.
Figure 6:
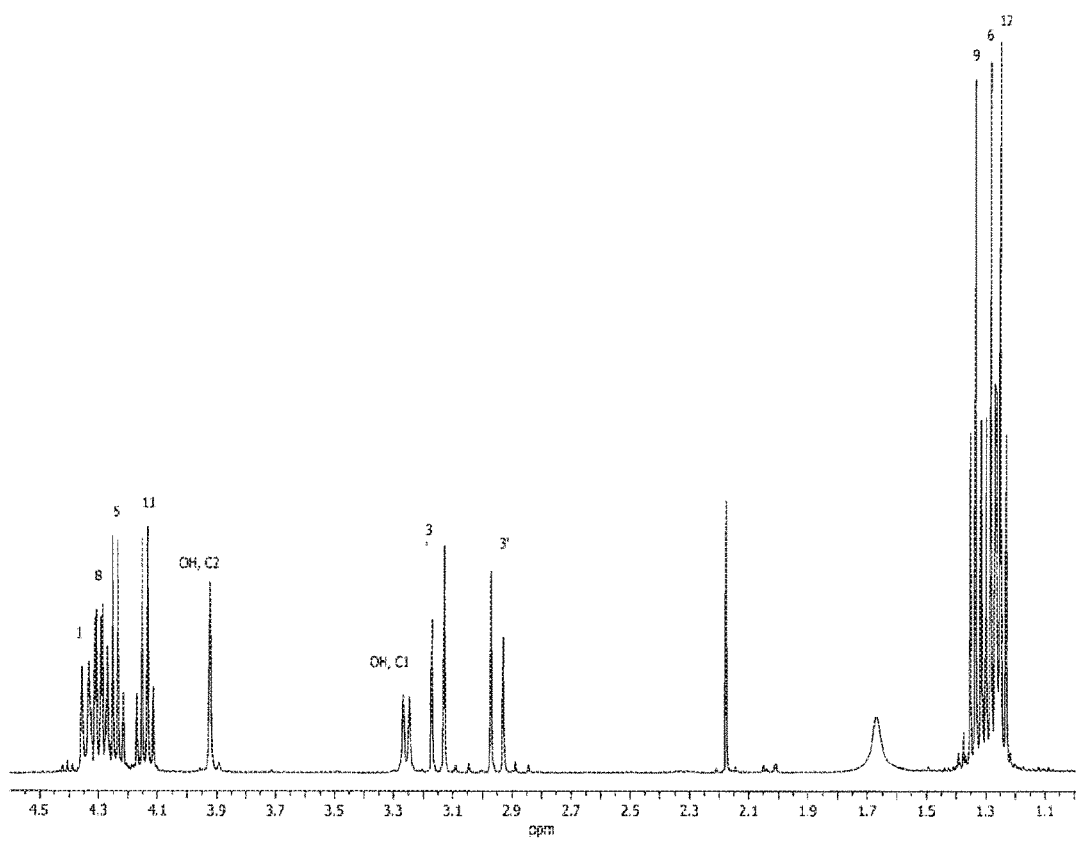
FIG. 6 shows nuclear magnetic resonance spectrum (NMR) of PROTON (1H) of ethyl triester of hydroxy citric acid in acetone-d6.

Example 5: Nuclear Magnetic Resonance (NMR) of PROTON (1H) of the Fractions Obtained by Re-Chromatography of the Extracts of Calyces of Jamaica Several PROTON NMR spectra of the 30 fractions showed similar NMR spectra so it was concluded that several of them were the same compounds. However, it was possible to isolate and identify six compounds: *Hibiscus* acid, the mono ester methyl of *Hibiscus* acid, di-ester methyl of *Hibiscus* acid, mono ester ethyl of *Hibiscus* acid, di-ester ethyl of *Hibiscus* acid; and tri-ethyl ester of hydroxycitric acid (FIGS. 1 to 6).

Example 6: The Chemical Structure of *Hibiscus* Acid and Derivatives is Shown

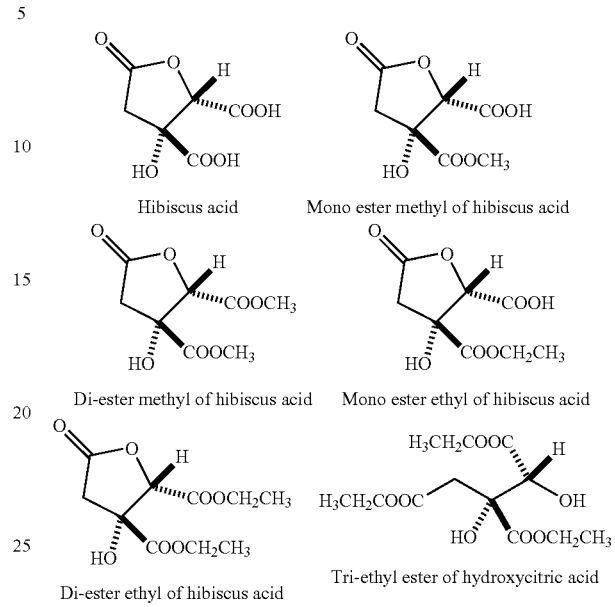

Example 7: Antimicrobial Effect of *Hibiscus* Acid and Derivatives

It was found that all the compounds had antimicrobial effect against the control (Tables 3). The maximum zone of inhibition was obtained with the *Hibiscus* acid and the lowest with ethyl triester of hydroxycitric acid. It was also observed that the most sensitive microorganism was *V. Cholerae*.

It should be noted that the strain of *S. Typhimurium* R+ used in the study was resistant to 14 antibiotics and was isolated from raw meat in our laboratory. And as seen in Table 3, the 6 compounds examined had an antimicrobial effect on this multiresistant strain to antibiotics.

TABLE 3

Zones of inhibition (mm)[1] of the development in culture medium of 13 different microorganisms caused by hibiscus acid and its derivatives

| [2]Compound | A* | B | C | D | E | F | G | H | I | J | K | L | M |
| --- | --- | --- | --- | --- | --- | --- | --- | --- | --- | --- | --- | --- | --- |
| 1 | 10 | 12 | 10 | 11 | 12 | 10 | 10 | 10 | 10 | 10 | 10 | 10 | 14 |
| 2 | 10 | 10 | 10 | 10 | 10 | 10 | 10 | 10 | 8 | 8 | 10 | 8 | 12 |
| 3 | 8 | 8 | 8 | 8 | 8 | 8 | 8 | 8 | 8 | 8 | 8 | 8 | 10 |
| 4 | 6 | 6 | 6 | 6 | 6 | 6 | 6 | 6 | 6 | 6 | 6 | 6 | 8 |
| 5 | 6 | 6 | 6 | 6 | 6 | 6 | 6 | 6 | 6 | 6 | 6 | 6 | 8 |
| 6 | 5 | 5 | 5 | 5 | 5 | 5 | 5 | 5 | 5 | 5 | 5 | 5 | 6 |
| 7 | 0 | 0 | 0 | 0 | 0 | 0 | 0 | 0 | 0 | 0 | 0 | 0 | 0 |

[1]Average of four repetitions
[2]Compound: 1 = hibiscus acid; 2 = mono ester methyl of hibiscus acid; 3 = di-ester methyl of hibiscus acid; 4 = mono ester ethyl of hibiscus acid; 5 = di-ester ethyl of hibiscus acid; 6 = tri-ethyl ester of hydroxycitric acid; 7 = distilled water (control).
*Type of microorganism: A = *E. coli* O157H7; B = *E. coli* enteroinvasive; C = *E. coli* enterotoxigenic; D = *E. coli* enteropathogenic, E = *Salmonella Typhimurium* R+; F = *Salmonella choleraesuis* ; G = *Shigella sonnei*; H = *Shigella flexneri*; I = *Listeria monocytogenes*; J = *L. monocytogenes* scott A; K = *Staphylococcus aureus*; E = *Pseudomonas aeruginosa*; M = *V. cholerae* O1.

Therefore, the six compounds of the present invention are an excellent antimicrobial alternative that had not been reported. In this sense, the compounds described herein, allow the inhibition of pathogenic bacteria resistant and not resistant to antibiotics.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

BIBLIOGRAHIC REFERENCES

1. Baraona, C. M. & Sancho, B. E. (1998). Apple, Peach, Strawberry and Blackberry. Special Fruit Growing 6. Editorial EUNED: Barcelona.
2. Castro-Rosas, J., Escartin, E. F., 2000. Survival and growth of *V. cholerae* 01, S. fyp/7/and £ co//0157: H7 in alfalfa sprouts. J. Food Sci. 65: 162-165.
3. Cruz-Gálvez, A. M., C. A. Gómez-Aldapa, J. R. Villagómez-Ibarra, N. Chavarría-Hernández, J. Rodríguez-Baños, E. Rangel-Vargas, and J. Castro-Rosas. 2013. Antibacterial effect against foodborne bacteria of plants used in traditional medicine in central Mexico: Studies in vitro and in raw beef. Food Control. 32: 289-295.
4. Fernández E. E. 2000. Microbiology and food safety. Autonomous University of Queretaro. Mexico.
5. Rural Finance. 2010. Mango monograph. Pp. 2. Mexico
6. Gutiérrez-Alcántara E. J., Gómez-Aldapa A. C., Román-Gutiérrez A. D., Rangel-Vargas E., González-Olivares L. G. and Castro-Rosas, J. 2015. Antimicrobial activity of roselle *Hibiscus sabdariffa* calyx extracts on culture media and carrots against multidrug-resistant *Salmonella* strains isolated from raw. J. Food Safety. Accepted.
7. Howard, C, J. Mass, C. Chandler and E. Albregts. 1992. Anthracnose of strawberry caused by *Colletotrichum* complex in Florida. Plant diseases. 7: 976-981.
8. Minaya, A. 1999. Mango in Peru and its links to the international market. Andean regional center. Pp. 99-104
9. Morales-Cabrera, M., Hernández-Morales, J., Leyva-Rúelas, G., Salinas-Moreno, Y., Soto-Rojas, L. and Castro-Rosas, J. 2013. Influence of variety and extraction solvent on antibacterial activity of roselle (*Hibiscus sabdariffa* L.) calyxes. J. Med. Plan. Res. 7 (31), 2319-2322
10. Secretariat of Agriculture, Livestock, Rural Development, Fisheries and Food (SAGARPA). 2009. Agri-Food and Fisheries Information Service. Available at: http://www.siap.gob.mx/ventanalM.php?idCat=173 & url=w4.siap.gob.mx/App Status/Monographs/Monografias2/Fresa.html. Retrieved on Mar. 24, 2014.
11. Secretariat of Agriculture, Livestock, Rural Development, Fisheries and Food (SAGARPA). 2013. Atlas agroalimentario 2013. Available at: http://vvww.siap.sagarpa.gob.mx/atlas2013/index.html. Retrieved on Apr. 24, 2014.
12. Tajkarími MM, Ibrahim SA, and Cliver DO. 2010. Antimicrobial herb and spice compounds in food. Food Control. 21: 1199-1218.

What is claimed is:

1. An antimicrobial composition consisting of:
    a *Hibiscus* acid as an antimicrobial agent in a concentration between 0.01 to 10% weight; and
    polysorbate and water in a ratio of 80:20.

* * * * *